US011698305B1

(12) United States Patent
Zhang et al.

(10) Patent No.: US 11,698,305 B1
(45) Date of Patent: Jul. 11, 2023

(54) SYSTEM AND METHOD FOR AUTOMATIC MEASUREMENT AND RECORDING (71) Applicant: Squadle, Inc., Cambridge, MA (US)

(72) Inventors: Le Zhang, Allston, MA (US); William K. Chen, Medford, MA (US)

(73) Assignee: Squadle, Inc., Cambridge, MA (US)

( * ) Notice: Subject to any disclaimer, the term of this patent is extended or adjusted under 35 U.S.C. 154(b) by 130 days.

(21) Appl. No.: 17/114,302

(22) Filed: Dec. 7, 2020

Related U.S. Application Data

(63) Continuation of application No. 15/890,697, filed on Feb. 7, 2018, now Pat. No. 10,859,443, which is a
(Continued)

(51) Int. Cl.
*G01K 1/02* (2021.01)
*G01K 1/022* (2021.01)
*G01D 9/32* (2006.01)
*G01N 33/02* (2006.01)
*G01K 7/02* (2021.01)
(Continued)

(52) U.S. Cl.
CPC .............. *G01K 1/022* (2013.01); *G01D 9/32* (2013.01); *G01K 7/02* (2013.01); *G01K 7/22* (2013.01); *G01N 33/02* (2013.01); *G08C 17/02* (2013.01); *G01K 2207/04* (2013.01)

(58) Field of Classification Search
CPC ............ G01K 1/02; G01K 1/022; G01K 7/02; G01K 7/22; G01K 2207/04; G01D 9/32; G01N 33/02; G08C 17/02
See application file for complete search history.

(56) References Cited

U.S. PATENT DOCUMENTS

| 4,493,980 A | 1/1985 | Payne et al. |
| 4,692,596 A | 9/1987 | Payne |

(Continued)

FOREIGN PATENT DOCUMENTS

CN 104204219 A * 12/2014 ............ C12M 41/46

OTHER PUBLICATIONS

Dieter K Schroder, Surface voltage and surface photovoltage: history, theory and applications, in final form Oct. 19, 2000, accepted for publication Dec. 14, 2000, 16 pages.
(Continued)

*Primary Examiner* — Tung S Lau
(74) *Attorney, Agent, or Firm* — Fish & Richardson P.C.

(57) ABSTRACT

A method and apparatus for automatically measuring and storing a various measured values of an item, or a sequence of measured values of one or more item(s) suitable for single-handed use by a user. In particular, the present invention relates to a mobile computing device with one or more sensors for determining when to measure and record a particular value of one or more items. The mobile computing device may automatically measure the values based on sensing a change in the temperature value or through using proximity as detected by one or more onboard sensors. Additionally, the mobile computing device may automatically measure the values based on coming within range of an external proximity device. In response to automatically measuring the values, the measured values are stored along with additional information for record keeping purposes.

20 Claims, 8 Drawing Sheets

Related U.S. Application Data continuation of application No. 15/395,270, filed on Dec. 30, 2016, now Pat. No. 9,921,112, which is a continuation of application No. 15/010,792, filed on Jan. 29, 2016, now Pat. No. 9,534,938.

(60) Provisional application No. 62/110,065, filed on Jan. 30, 2015.

(51) Int. Cl.
  *G08C 17/02* (2006.01)
  *G01K 7/22* (2006.01)

(56) References Cited

U.S. PATENT DOCUMENTS

| | | | |
|---|---|---|---|
| 5,062,066 A | 10/1991 | Scher et al. | |
| 5,371,842 A * | 12/1994 | Easton | G01R 13/0227 345/442 |
| 5,717,421 A * | 2/1998 | Katakura | G09G 3/3629 345/98 |
| 5,844,684 A | 12/1998 | Maris | |
| 5,900,801 A | 5/1999 | Heagle et al. | |
| 5,939,974 A | 8/1999 | Heagle et al. | |
| 6,133,555 A | 10/2000 | Brenn | |
| 6,275,779 B1 * | 8/2001 | Pohle | G01K 1/02 374/102 |
| 6,817,757 B1 | 11/2004 | Wallace | |
| 6,856,247 B1 | 2/2005 | Wallace | |
| 6,904,370 B1 | 6/2005 | Levinson et al. | |
| 7,026,929 B1 | 4/2006 | Wallace | |
| 7,251,290 B2 | 7/2007 | Rashev | |
| 7,834,839 B2 * | 11/2010 | Muto | G09G 3/3611 345/87 |
| 9,534,938 B1 | 1/2017 | Zhang et al. | |
| 9,625,327 B1 | 4/2017 | Bernstein | |
| 9,818,373 B2 * | 11/2017 | Ohta | G09G 5/10 |
| 9,921,112 B2 | 3/2018 | Zhang et al. | |
| 2002/0147396 A1 | 10/2002 | Fleury | |
| 2004/0004456 A1 | 1/2004 | LeBa et al. | |
| 2005/0043900 A1 | 2/2005 | Franda | |
| 2005/0261991 A1 | 11/2005 | Kennamer | |
| 2007/0255163 A1 * | 11/2007 | Prineppi | G01D 9/007 600/549 |
| 2008/0036727 A1 * | 2/2008 | Muto | G09G 3/3611 345/101 |
| 2008/0043809 A1 | 2/2008 | Herbert | |
| 2008/0158443 A1 * | 7/2008 | Shiomi | G09G 3/3648 345/589 |
| 2010/0076712 A1 | 3/2010 | Aoki et al. | |
| 2012/0078659 A1 | 3/2012 | Ashrafzadeh | |
| 2013/0043393 A1 | 2/2013 | Heaven et al. | |
| 2014/0273858 A1 | 9/2014 | Panther et al. | |
| 2014/0349267 A1 | 11/2014 | Thornton | |
| 2015/0279324 A1 * | 10/2015 | Ohta | G09G 3/3283 345/82 |
| 2016/0037566 A1 | 2/2016 | Jakusovszky et al. | |
| 2016/0377457 A1 | 12/2016 | Zhang et al. | |
| 2017/0108382 A1 | 4/2017 | Zhang et al. | |
| 2018/0075798 A1 * | 3/2018 | Nho | G09G 3/32 |

OTHER PUBLICATIONS

Gelatin Manufactures Institutes of America, Standard Testing Methods for Edible Gelatin, Jul. 2013, 28 pages.

Non-Final Office Action in U.S. Appl. No. 15/265,611, dated Mar. 13, 2017, 13 pages.

Stephanie Bell , A beginner's guide to humidity measurement, Oct. 2011, 29 pages.

TA.XTPlus Texture Analyzer, download Jul. 12, 2016, 5 pages, http://texturetechnologies.com/texture-analyzers/TA-XTPlustexture-analyzer.php.

* cited by examiner

SYSTEM AND METHOD FOR AUTOMATIC MEASUREMENT AND RECORDING

CROSS-REFERENCE TO RELATED APPLICATIONS

This application is a continuation of U.S. application Ser. No. 15/890,697 filed Feb. 7, 2018, which is a continuation of U.S. application Ser. No. 15/395,270, filed Dec. 30, 2016, which is a continuation of U.S. application Ser. No. 15/010,792, filed Jan. 29, 2016, which claims priority from and the benefit of U.S. Provisional Patent Application No. 62/110,065, filed Jan. 30, 2015. The entire contents of the prior applications are incorporated by reference herein.

TECHNICAL FIELD

This document relates to measuring and storing measured values of an item or space, or a sequence of measured values of one or more item(s) or space(s) suitable for single-handed use by a user. In particular, the present invention relates to repeated automatic measuring and recording measurements of one or more items or spaces, for example, in a food service environment.

BACKGROUND

Generally, employees of restaurants routinely take measurements of different items and spaces utilized in operating the restaurant. For example, the temperature readings of a number of cooked and/or raw food items are routinely measured to ensure that the food is being stored at a safe and desired temperature. The temperature readings are taken in accordance with the food safety regulations established by the U. S. Food and Drug Association (FDA) or other regulations established by the restaurant for health and liability reasons. Typically the temperature readings must be done on a regular basis throughout the day, and the temperatures must be logged so that they can be viewed later. Most commonly, this is done using a thermometer, writing utensil, and paper logbook, causing the employee to have to juggle at least three instruments plus the food item that needs to be tested. More tech savvy restaurants have adopted digital logging systems, consisting of a tablet or a computer, paired with a wirelessly tethered thermometer. However, this method causes the employee to have to juggle two instruments plus the food to complete the temperature readings. Accordingly, the traditional measuring and logging used in the restaurant industry is prone to errors and inconsistency, particularly for quick service restaurants, which have many repetitive temperature or other measurement-taking tasks.

Further, measurement devices in the food industry are generally not able to determine when to take a measurement, what type of sample is being measured, or whether a measurement is within a valid or appropriate range for the sample being measured. As a result, many prior devices may fail to acquire measurements at appropriate times, produce inaccurate measurements or measure incorrect parameters, produce incorrect data or data that is not appropriate for the sample being measured, or may fail to record or may inaccurately record measured values.

SUMMARY

There is a need for a fast reliable measuring and recording system and method in the food industry. The present invention is directed toward further solutions to address this need, in addition to having other desirable characteristics. Specifically, the invention consists of a probe device that is the sole instrument required to take the necessary measurements of items and spaces related to restaurant operation, the probe device being entirely operable with one hand. In addition, the present invention includes a method to streamline the process such that the probe device can automatically sense when to take the desired measurement, so that no human input is required in real time to trigger the recording of the desired measurement.

As noted above, in general, measurement devices in the food industry are not able to determine when to take a measurement, what type of sample is being measured, or whether a measurement is within a valid or appropriate range for the sample being measured. As a result, many prior devices may produce inaccurate data or produce data that is not recorded or is inaccurately recorded. As discussed below, in some implementations, a device can storing data corresponding to different sample types, allowing the device to determine different. In some implementations, a device can automatically determine when to initiate a measurement cycle, for example, in response to detecting changes in a measured characteristic or in response to detecting a position or proximity to a target sample. In some implementations, a device can determine when an appropriate measurement value has been acquired and automatically record the value, for example, when the device determines a steady state value within a predetermined range is detected.

In one general aspect, a method includes: receiving, by the probe device, data that indicates a sample type to be measured; accessing, by the probe device, data indicating a predetermined range of sample physical measurement values corresponding to the selected sample type; detecting, by the probe device, an ambient measurement value within a predetermined range of ambient measurement values that is different from the predetermined range of sample physical measurement values; after detecting the ambient measurement value, detecting, by the probe device, a change in the measurement value away from the ambient measurement value; after detecting a change in the measurement value away from the ambient measurement value, determining, by the probe device, that a steady state measurement value has been achieved within the predetermined range of sample physical measurement values; and automatically recording, by the probe device, the steady state measurement value based on determining that the steady state measurement value has been achieved within the predetermined range of sample physical measurement values.

Implementations may include one or more of the following features. For example, the method may include accessing, by the probe device, data indicating multiple different sample types; and providing, by the probe device, a user interface indicating the multiple different sample types, the respective sample types each having a corresponding predetermined range of physical measurement values. Receiving data that indicates a sample type to be measured can include receiving user input that selects a sample type from among the multiple sample types indicated by the user interface. Accessing the data indicating multiple different sample types can include accessing data indicating multiple different food items or food preparation spaces, wherein each of the different food items or food preparation spaces has a corresponding range of sample physical measurement values. Accessing the data indicating the predetermined range of sample physical measurement values corresponding to the selected sample type can include accessing data indicating a temperature range corresponding to a selected food item or food preparation space. Detecting the change in the measurement value can include: accessing, by the probe device, data indicating a threshold amount corresponding to the physical measurement value; after detecting the ambient measurement value, detecting a second measurement value in response to placement of a sensor coupled to the probe device in the target sample; and determining that the second measurement value differs from the ambient measurement value by at least the threshold amount.

Implementations may include one or more of the following features. For example, detecting the change in the measurement value can include: accessing, by the probe device, data indicating the predetermined range of ambient measurement values; after detecting the ambient measurement value, detecting a second measurement value that is outside the predetermined range of ambient measurement values; and determining that the second measurement value is outside the predetermined range of ambient measurement values. The sample physical measurement value is a measure of a characteristic selected from the group consisting of temperature, pH, color, density, specific gravity, humidity, and level of total polar materials (TPM). Automatically recording the steady state measurement value is performed without receiving user input instructing the steady state measurement to be made and without receiving user input instructing recording of the steady state measurement value. In some implementations, the probe device is a mobile phone in communication with a sensor. The method can include, in response to detecting the change in the measurement value away from the ambient measurement value, providing, by the probe device, output indicating that a measurement cycle to acquire a steady state measurement value has been initiated; and in response to determining that a steady state measurement value has been achieved within the predetermined range of sample physical measurement values, providing, by the probe device, output indicating that the measurement cycle has been completed.

Implementations may include one or more of the following features. For example, automatically recording the steady state measurement value can include recording a time that the steady state measurement was detected, an identifier for the sample type, a geographic location where the steady state measurement value was detected, or a user identifier for a user taking the steady state measurement. The method may include outputting, by the probe device, (i) an ordered checklist indicating a plurality of measurements to be performed using the probe device, (ii) a duration of a measurement cycle for acquiring the steady state measurement value, or (iii) a time when a subsequent measurement is scheduled to be performed. The method may include determining, by the probe device, that the probe device is within a predetermined level of proximity to the target sample; and initiating a measurement cycle to obtain the steady state measurement value in response to determining that the probe device is within the predetermined level of proximity to the target sample. Determining that the probe device is within the predetermined level of proximity can include: receiving, by the probe device, sensor data indicating proximity of the probe device to the target sample or a transmission from a device in proximity to the target sample; and determining, by the probe device, that that the probe device has been inserted into a sample item or space to a predetermined depth of a sample item or space of the target sample based on the received sensor data or received transmission. Receiving data that indicates the sample type to be measured can include: receiving, by the probe device, an indication of the sample type from a near field communication tag, an optical machine-readable code, a wireless beacon, or a connected appliance. The method can include initiating a measurement cycle to obtain the steady state measurement value in response to receiving the indication of the sample type.

Implementations may include one or more of the following features. For example, automatically recording the steady state measurement value can include recording the steady state measurement value locally at the probe device. Automatically recording the steady state measurement value can include transmitting the steady state measurement value over a network to a server system for storage by the server system. A measurement cycle comprising a series of multiple measurements of a characteristic of the target sample can be initiated by the probe device in response to detecting the change from the ambient measurement value or determining that the probe device or an associated sensor is in proximity to the target sample. The measurement cycle can have a predetermined duration and include multiple measurements taken at a predetermined interval. The probe device may determine that a level of variation among the measurement values acquired during the measurement cycle exceeds a predetermined threshold, and initiate a second measurement cycle and/or provide an alert indicating that a steady state measurement value is not achieved in response. The alert from the probe device may provide an output instructing a user to continue a measurement for an indicated period of time. The probe device may determine that a steady state measurement value is not within the predetermined range of values corresponding to the sample type of the target sample. In response, the probe device may initiate another measurement cycle and/or provide an alert indicating that the steady state measurement value is outside the predetermined range values corresponding to the sample type of the target sample. The probe device may indicate the steady state measurement value, the predetermined range, and/or a difference between the steady state measurement value and the predetermined range. The probe device may provide an output indicating a scheduled measurement to be acquired. The probe device may be in communication with a thermocouple sensor, and the thermocouple sensor may provide data indicating the measurement values. The thermocouple sensor may be integrated into the computing device. The thermocouple sensor may be included in a peripheral device that is connected to the computing device, for example, through a wireless or wired connection. The probe device or a probe element may comprise hydrophobic elements.

Other embodiments of this and other aspects include corresponding systems, apparatus, and computer programs, configured to perform the actions of the methods, encoded on machine-readable storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

In another general aspect, a system for automatically measuring and recording a sample physical measurement value of a target sample is provided. The system may include a mobile probe device comprising a sensor in communication with a computing hardware device. The computing hardware device includes a selector indicating a sample type, the sample type having a predetermined range of sample physical measurement values. The computing hardware device is configured to determine when the sensor has acquired a steady state measurement value within the predetermined range of sample physical measurement values. In response to the determination, the computing hardware device is configured to automatically record the steady state measurement value.

BRIEF DESCRIPTION OF THE DRAWINGS

These and other characteristics of the present invention will be more fully understood by reference to the following detailed description in conjunction with the attached drawings.

DETAILED DESCRIPTION

An illustrative embodiment of the present invention relates to a system suitable for automatically measuring and recording a value of one or more items or spaces. In particular, the present invention relates to a probe device configured as a computing hardware device in communication with one or more sensors which is capable of determining when to measure and record a particular value of one or more items or spaces. Advantageously, the present invention enables the measurement process to be performed single-handedly, such that a user is not required to juggle multiple items to obtain a measurement. For example, a user may automatically take and record a temperature of one or more food items during their preparation. Accordingly, the food items may be prepared without the danger of contamination due to the handling of multiple objects typically used to perform the measurements and recordings. Additionally, the present invention eliminates the potential of human error when recording the measured values because the single-handed device automatically measures and records the value without requiring manipulation of the device as by a user as the measurement is taken. Particular embodiments of the invention have been described. Other embodiments are within the scope of the following claims. For example, the steps recited in the claims can be performed in a different order and still achieve desirable results.

A system 10 according to the present invention includes a probe device 12 that includes a computing hardware device 14 in communication with a sensor 16. The probe device 12 is configured to carry out the steps of measuring and recording values in accordance with the present invention. Specifically, the probe device 12 is in communication with one or more sensor(s) 16. The probe device 12 is configured to determine when to take a measured value of an item or space, measure that value to determine when a steady state value is achieved, and subsequently record the steady state measured value without receiving or requiring instructions from a user operating the probe device 12. The automatic determination of when to take a measurement may include determining when the probe device 12 has been inserted into an item, or a space, to be measured. The determination of the insertion of the probe device 12 into an item or space is performed automatically, such that a user's instructions to take a measurement are not needed. The determination of when a measurement value should be taken may be performed by detecting when a change of measurement value(s) at the sensor 16 has occurred, triggering instructions to take the measurement. Additionally, the use of proximity sensors 18 may be implemented such that once the probe device 12 comes within range of one of the proximity sensors 18, instructions to take the measurement value(s) are triggered. As would be appreciated by one of skill in the art, these methods may be used in exclusivity or in combination. Once the measurement value is taken and a steady state of that measured value has been determined, the measured value may be automatically recorded in a format useful to the user (e.g., recorded in a logging application). Accordingly, the present invention enables the user to use a single hand to insert a probe into an item to automatically take and record a measured value of that item, while requiring no additional action by the user.

FIGS. 1 through 5, wherein like parts are designated by like reference numerals throughout, illustrate an example embodiment or embodiments of automatically measuring and recording temperature(s) of one or more items, according to the present invention. Although the present invention will be described with reference to the example embodiment or embodiments illustrated in the figures, it should be understood that many alternative forms can embody the present invention. One of skill in the mi will additionally appreciate different ways to alter the parameters of the embodiment(s) disclosed, such as the size, shape, or type of elements or materials, in a manner still in keeping with the spirit and scope of the present invention.

Figure 1:
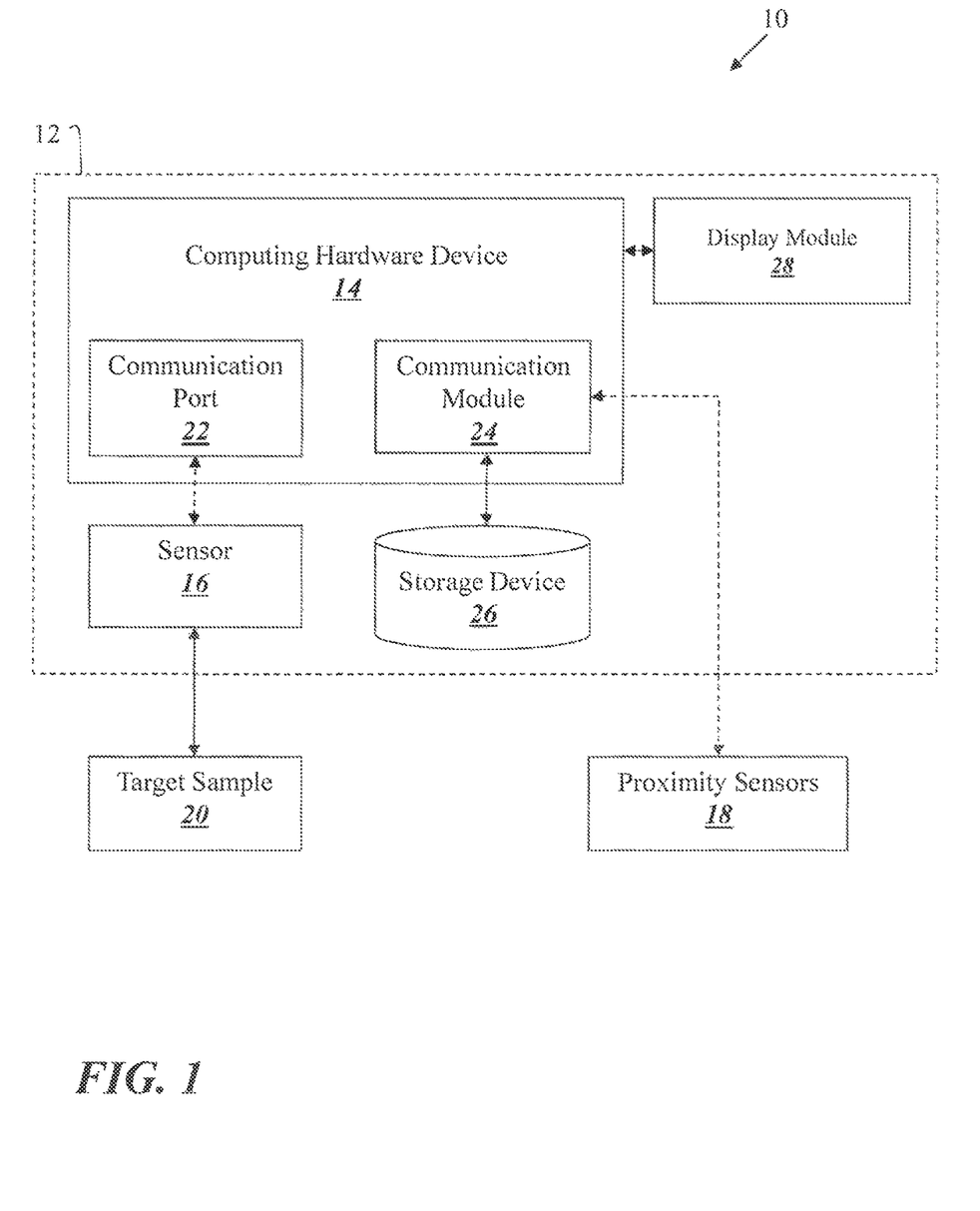
FIG. 1 illustrates a system for obtaining a sample physical measurement value of a target sample using a probe device in accordance with one embodiment of the present invention.

FIG. 1 depicts a high level architecture of implementing processes in accordance with aspects of the present invention. Specifically, FIG. 1 depicts the system 10 for automatically measuring and recording a sample physical measurement value of a target sample 20 using the probe device 12. The probe device 12 includes computing hardware device 14, the computing hardware device 14 in communication with at least one sensor 16. The computing hardware device 14 may be a general purpose computer or a specialized computer system configured to automatically measure and record a temperature of one or more items. As would be appreciated by one of skill in the art, the computing hardware device 14 may include a single computing device, a collection of computing devices in a network computing system, a cloud computing infrastructure, or a combination thereof. For example, the computing hardware device 14 may be a mobile computing device, such as a smartphone, a tablet, a laptop, personal digital assistant (PDA), smartwatch, or other mobile computing device. In some implementations, the computing hardware device 14 is a handheld device having a processor and a communications interface for communicating with at least one sensor. The computing hardware device 14 may include one or more communication ports 22. As would be appreciated by one of skill in the art, the communication port 22 may be configured to input, output, and/or store data from another computing device. For example, the communication port 22 may include a Universal Serial Bus (USB), a mini USB, a micro USB, docking port, etc.

Additionally, the computing hardware device 14 may include wired or wireless a communication module 24 configured to communicate with a local or cloud server. For example, the communication module 24 may include an antenna to enable wireless communications (e.g., radio frequency (RF), Bluetooth, Wi-Fi, etc.). In accordance with an example embodiment of the present invention, the computing hardware device 14 may be configured to use the communication module 24 to establish a connection and communicate over telecommunication network(s). As would be appreciated by one of skill in the art, the telecommunication network(s) may include any combination of known networks. For example, the telecommunication network(s) may be combination of a mobile network, WAN, LAN, or other type of network. The telecommunication network(s) may be used to exchange data between the computing hardware device 14 and other computing devices in accordance with embodiments of the present invention. Similarly, the communication port 22 may be used to exchange data with another computing device over a wired connection. In accordance with an example embodiment, the computing hardware device 14 may use the communication module 24 and/or telecommunication network(s) to exchange data with a storage device 26. As would be appreciated by one of skill in the art, the storage device 26 may be a local storage device resident on the probe device 12 or may be a remote storage device 26. For example, the computing hardware device 14 may be connected to a local disk drive, a remote database facility, a virtual database, or a cloud computing storage environment. As one of skill in the art will appreciate, although reference is made herein to a single storage device 26, the storage device 26 may be implemented across multiple logically connected different storage devices 26, which can be locally or remotely coupled. Similarly, the storage device 26 may include any combination of computing devices configured to store and organize a collection of data.

Continuing with FIG. 1, the computing hardware device 14 may communicate with a display module 28 on the probe device 12 to provide a graphical user interface (GUI) to display information to the user about a current item of interest and potential metadata about the item of interest (e.g., an acceptable temperature ranges). As would be appreciated by one of skill in the alt, the display module 28 may be integrated on a peripheral device including the one or more sensors 16 or presented on the computing hardware device 14. Advantageously, the display module 28 may al so be configured to receive input from the user. For example, the display module 28 may be a capacitive and/or resistive touchscreen. As would be appreciated by one of skill in the art, the user may also send input to the computing hardware device 14 through the use of mechanical, resistive, and/or capacitive buttons. In accordance with an example embodiment of the present invention, the one or more sensors 16 may include a combination of hydrophobic elements or coatings and Ultraviolet (UV) light or antimicrobials. For example, the hydrophobic elements or coatings may be included throughout the body of the one or more sensors 16 and/or the probe device 12 or select portions thereof. Accordingly, the use of hydrophobic and UV/antimicrobial environment elements minimize or remove the need for a user to clean the device with a wipe after each use.

In operation, the probe device 12 may be used to automatically determine when to collect measured data, measure the data, and record the measured data without receiving or requiring real time instructions from a user. Furthermore, the probe device 12 of the present invention may utilize any combination of measurement instruments known in the art as the one or more sensors 16 to measure various types of data for one or more sample items. As would be appreciated by one of skill in the ail, the probe device 12 may include the one or more sensors 16 in the form of instruments configured to measure temperature, pH, color, density, specific gravity, humidity, a level of total polar materials (TPM), etc. Once a measurement has been taken by the one or more sensors 16 of the probe device 12, the corresponding measured data may be stored (e.g., on the storage device 26) for record keeping purposes. For example, the probe device 12 may include a thermometer as the one or more sensors 16 for measuring the temperature of various food items and/or food preparation items. Advantageously, the probe device 12 may be used with a single hand of a user and automatically determines when to take a measurement, such that no human interaction is required to trigger the measuring and/or recording of the measured data (e.g., such as temperature, or the like) for the one or more target sample items or spaces. For example, the computing hardware device 14 automatically detects when the one or more sensors 16 of the probe device 12 have been inserted into a sample item or space for measurement and then triggers instructions for measurements to be taken by the probe device 12 and subsequently recorded in the storage device 26. As would be appreciated by one of skill in the art, the measured data may be stored locally on the probe device 12, on a centralized computing system (e.g., a restaurant management system), and/or on a remote database (e.g., storage device 26). In accordance with an example embodiment, the centralized computing system may be a computing system located on the same shared secure network as the probe device 12 and may be configured to manage a plurality of the probe devices 12 on the shared network. For example, the measured data may be transmitted to and stored on a tablet device running restaurant management software and is connected to the same local area network (LAN) as the probe device 12.

Figure 2A:
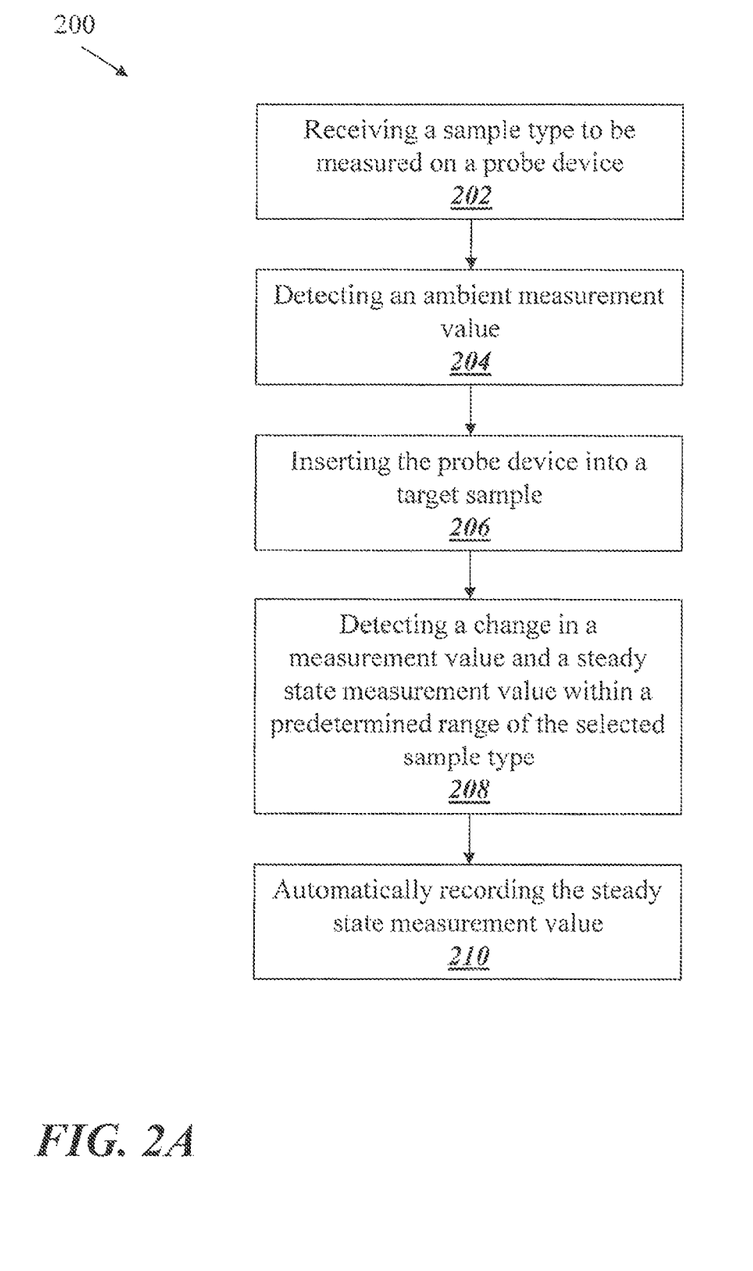
FIGS. 2A and 2B are illustrative flowcharts depicting a method for measuring and recording temperature of one or more items, in accordance with aspects of the present invention.
Figure 2B:
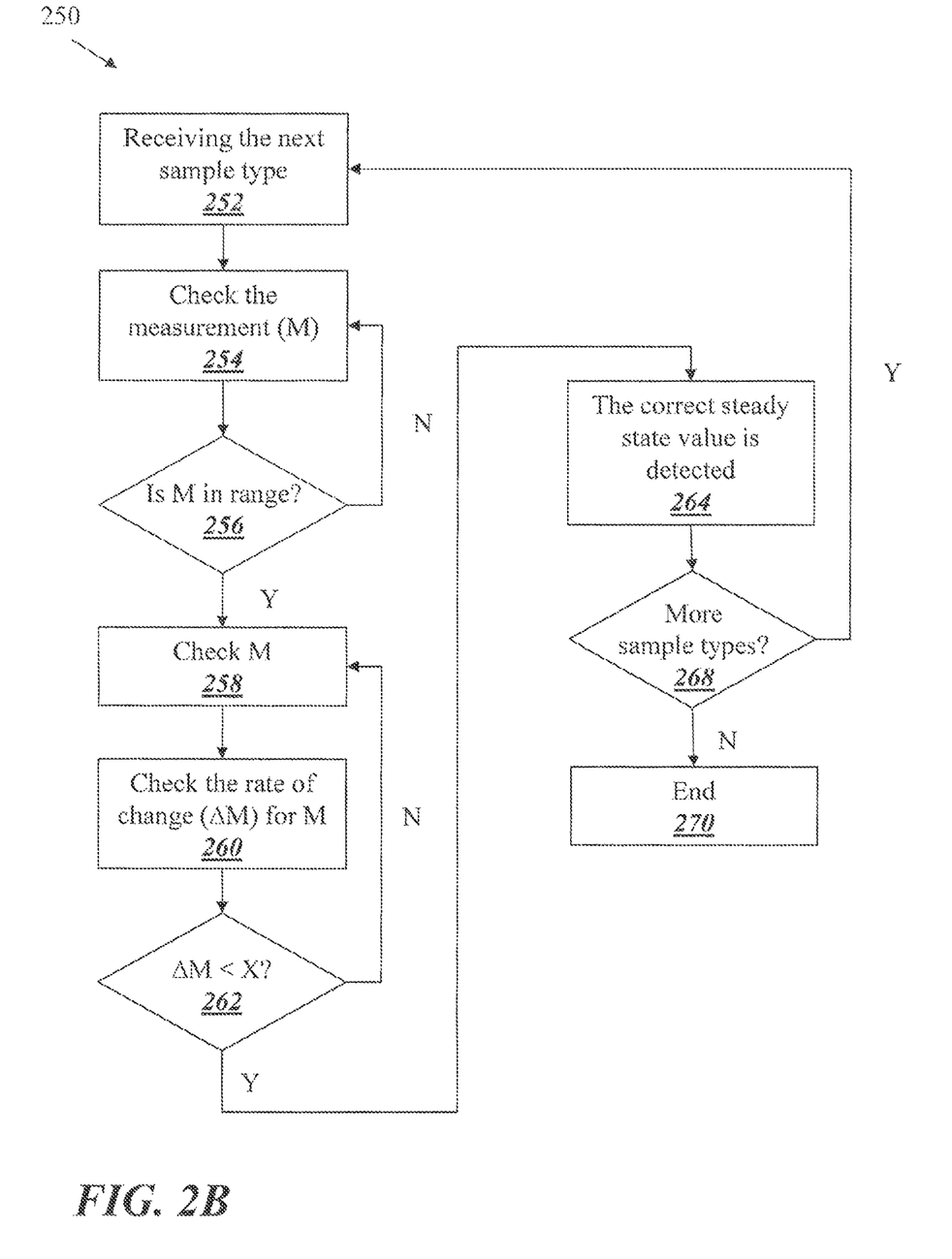
Figure 3:
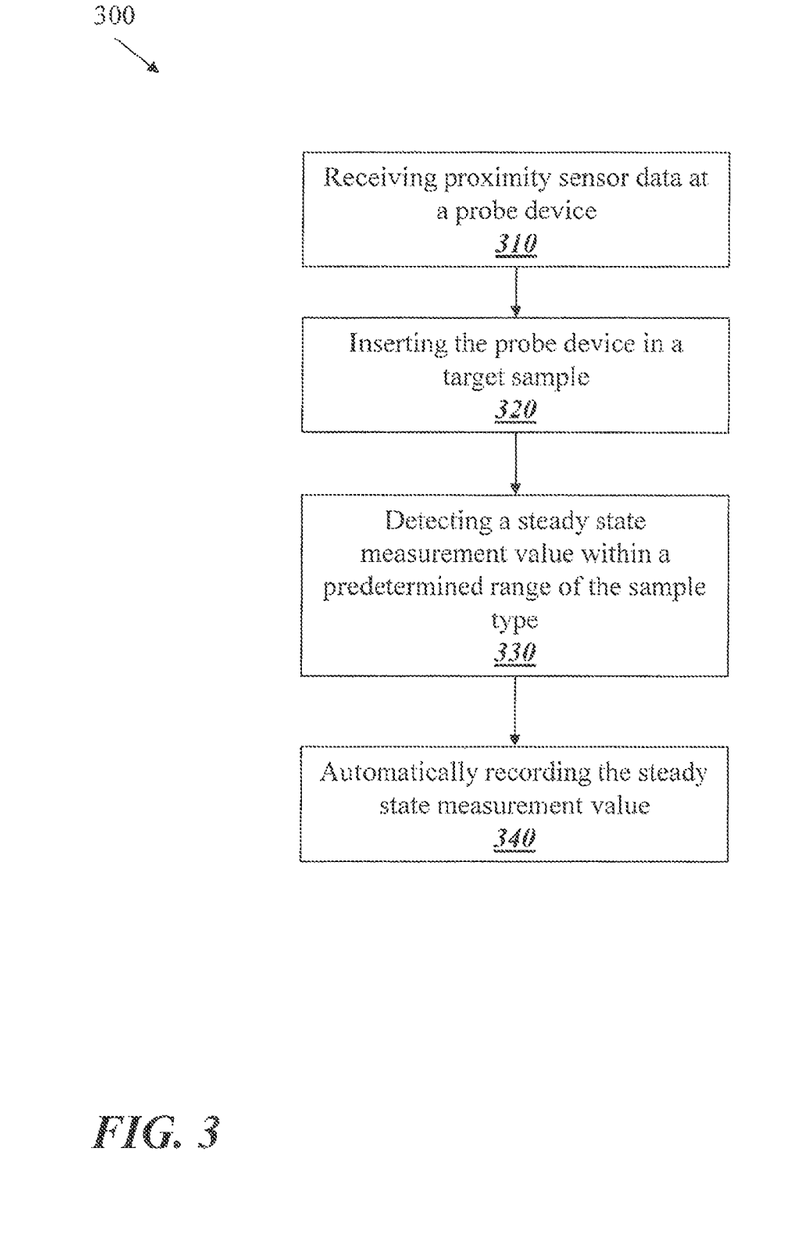
FIG. 3 is an illustrative flowchart depicting a method for measuring and recording a temperature of one or more items or spaces, in accordance with aspects of the present invention.

FIGS. 2A, 2B, and 3 show exemplary flow charts depicting implementation of the present invention. Specifically, FIG. 2A depicts an exemplary flow chart showing the operation of the probe device 12, as discussed with respect to FIG. 1. In particular, FIG. 2A depicts an example embodiment of the present invention in which the probe device 12 may automatically determine when to measure and record the measured values of a sample item or space. For example, the measured values may be taken and recorded using the combination of the computing hardware device 14 and the one or more sensors 16, as discussed with respect to FIG. 1.

At step 202, the automatic measuring performed by the probe device 12 may be initiated by receiving data that indicates a sample type. In accordance with an example embodiment of the present invention, the sample type data may be received through an indication from a user selecting sample items or spaces desired to be measured. As would be appreciated by one of skill in the art, a plurality of sample types may be presented to the user for selection from a collection of sample types stored in the storage device 26 or implemented by the computing hardware device 14. In accordance with an example embodiment of the present invention, the sample type indication may be received according to a predetermined list of sample types to be measured from the storage device 26. As would be appreciated by one of skill in the art, the list may indicate a set or sequence of different sample types to measure, and the user may follow the predetermined list of sample types when using the probe device 12. For example, the predetermined sample types may be presented to the user in as an ordered checklist. In accordance with an example embodiment of the present invention, the sample type may be received through receiving the sample type through an input at the computing hardware device (e.g., using the communication port 22 and/or the communication module 24). For example, the computing hardware device 14 may receive the sample type from a Near Field Communication (NFC) tag (e.g., an RFID tag) or by scanning an optical machine-readable code such as a two-dimensional or three dimensional barcode (e.g., barcode or Quick Reference (QR) code), etc. In accordance with an example embodiment of the present invention, the sample types may include various food items and food preparation items, such as poultry or the like, or may include spaces, such as oven or refrigerator temperatures or the like. In accordance with an example embodiment of the present invention, each of the sample types may have a corresponding predetermined range of the sample type's physical measurement values. For example, a predetermined range for poultry may be 165-170 degrees Fahrenheit. The ranges of measurement values can be different for each of multiple sample types. For example, a reference temperature threshold or range for chicken may be different from the reference temperature threshold or range for beef. The probe device may store data that indicates the range for each sample type, or may obtain the information from a server system through communication over a network.

At step 204, the probe device 12 may automatically detect an ambient measurement value. For example, the probe device 12 may include an internal thermistor for taking an ambient temperature. As would be appreciated by one of skill in the art, the thermistor may be used in conjunction with a thermocouple for measuring a temperature of an item accurately. For example, the computing hardware device 14 may use the measured ambient temperature and a polynomial lookup table (e.g., a NIST) to determine a measured temperature of a sample item. As would be appreciated by one of skill in the art, the temperature lookup may be performed by software, hardware, or a combination thereof. Additionally, the ambient measurement value may be determined by periodically measuring the ambient value of the space. As would be appreciated by one of skill in the art, the periodic measuring may be adjusted periodically in order to conserve battery life of the computing hardware device 14, one or more sensors 16, and/or the probe device 12. In accordance with an example embodiment of the present invention, the ambient measurement value may be determined by measuring the ambient value of a space upon initiating the one or more sensors 16, of the probe device 12.

At step 206, a user may physically insert the probe device 12, or at least the one or more sensors 16 into the selected target sample item or space. For example, the user may insert the temperature sensor (e.g., thermocouple) of the probe device 12 into a sample food item (e.g., poultry). As would be appreciated by one of skill in the art, the probe device 12, or the at least one or more sensors 16 may be configured to take a measurement without physically inserting the sensors 16 into the sample item or space. For example, a temperature may be taken of an item or space using an infrared (IR) or laser temperature sensor device. Additionally, the probe device 12 may display a measurement timer to the user instructing the user when the next measurement is going to be taken. For example, the probe device 12 may reflect that the next sample type is poultry and that the temperature will be taken in 15 seconds, to inform the user that the prober device or the one or more sensors 16 should be inserted (or aimed at if wireless temperature sensors are being used) into the poultry for the measurement.

At step 208, the probe device 12 may detect a change in a measurement value and then detect a steady state measurement value within a predetermined range of the received sample type (e.g., selected in step 202). For example, the probe device 12 may determine that the measurement value changed from the measured ambient temperature to a lessor or greater temperature (e.g., upon insertion into an item or space). The probe device 12 may measure an ambient temperature value of the space is 70 degrees Fahrenheit and upon insertion of the one or more sensors 16 into a sample item (e.g., poultry) detects that the measured temperature increased to 165 degrees Fahrenheit. The probe device 12 may also determine that the greater temperature is unchanging over a period of time (e.g., steady state) and is within a given threshold, such that the greater temperature falls within the predetermined range of the selected sample type (e.g., 165-170 degrees Fahrenheit for poultry). Similarly, as discussed with respect to the measured ambient value, the measured values of the sample items may be performed periodically. In accordance with an example embodiment of the present invention, a signal processing algorithm (e.g., as depicted in FIG. 2B) may be used to determine a change in the measured value comprising the difference between the ambient measurement value of a space and the measured value of the sample type after the insertion of the probe device 12. As would be appreciated by one of skill in the art, the signal processing algorithm may factor in the predetermined value range for a particular sample type being measured when determining the difference in the measured ambient value and the measured value of the sample item. For example, when the sample type is a refrigerated space and the predetermined temperature range for the space is less than a predefined ambient temperature range, the change in measurement value may be detected when the measurement value decreases below the ambient temperature range, or at least a predetermined threshold below the ambient temperature value detected.

At step 210, in response to determining a steady state measurement value falling within the predetermined range of the selected sample type (step 208), the probe device 12 may automatically record the steady state measurement value. For example, the steady state measurement value is recorded in the storage device 26 for the selected sample type (e.g., poultry). As would be appreciated by one of skill in the art, additional data and/or metadata may also be stored in the storage device 26. For example, the probe device 12 may also record a time at which the temperature was taken, the number and iteration of that particular sample type that has been taken, an employee identifier of the user taking the measurements, etc. Accordingly, any necessary restaurant logging data may be automatically measured and recorded in the storage device 26.

FIG. 2B depicts an example embodiment of the signal processing algorithm used in accordance with the present invention, (e.g., as described with respect to step 208 of FIG. 2A). In particular, the signal processing algorithm is depicted by the process 250 shown in FIG. 2B. At step 252, the signal processing algorithm is initiated upon reception of a next sample type item (e.g., a sample type as discussed with respect to FIGS. 1 and 2A). As would be appreciated by one of skill in the art, the sample type may be received automatically from a predetermined list or from an input from a user, as discussed with respect to step 202 of FIG. 2A. At step 254, a measurement value is taken of the sample type (e.g., a sample item or a space). As would be appreciated by one of skill in the art, the measurement value is taken by the one or more sensors 16. At step 256, a determination is made (e.g., by the computing hardware device 14) as to whether the measured value falls within a predetermined range of the received sample type (e.g., as discussed with respect to step 208 of FIG. 2A). For example, if the received sample type is poultry, and the predetermined range for poultry is 165-170 degrees Fahrenheit, then the computing hardware device 14 determines whether the measurement value falls within the range of 165-170 degrees Fahrenheit. If the measurement value falls within the predetermined range for the received sample type then the process advances to step 258. Otherwise, the process returns to step 254, and the measurement is taken again. In accordance with an example embodiment of the present invention, if the measurement value does not fall within the predetermined range, in addition to returning to step 254, an alert may be triggered and displayed to a user of the probe device 12. For example, the alert may convey to the user that the measured value is not within a predetermined range for that sample type and that the probe device 12 should stay inserted within the sample item until a measurement within the predetermined range is achieved.

At step 258, similarly to step 254, a measurement value is taken of the sample type. For the first iteration of step 260, the measurement values from steps 254 and 258 are compared to determine a rate of change of the measurements values (e.g., M (where M represents the measured value)). As would be appreciated by one of skill in the art, subsequent determinations of the rate of change (from the initial change of temperature) will compare the most recent sample measurement values (e.g., the last two measured values). For example, if the measured value from step 254 is 165 degrees Fahrenheit and the measured value from step 258 is 166 degrees Fahrenheit, then the rate of change is 1 degree per unit time between measurement samples. As would be appreciated by one of skill in the art, the measurements of values in steps 254 and 258 are may be made over a periodic basis, for example, at a predetermined interval. For example, the measurements may be taken about 3 seconds apart. For example, actions such as detecting proximity to a target sample (or an associated wireless beacon, appliance, or other device) can trigger the initiation of a measurement cycle. For example, a measurement cycle may include a series of 5 measurements taken 3 seconds apart. At the end of the measurement cycle the probe device determines whether to record the measurement (e.g., if a steady state value within the appropriate range for the sample type was achieved), to alert the user (e.g., if a steady state value outside the appropriate range was achieved), or to continue measurement by initiating a new measurement cycle (e.g., if variation between the measurements exceeded a threshold such that a steady state measurement value was not obtained).

At step 262, a determination is made (e.g., by computing hardware device 14) as to whether the rate of change is less than (e.g., <) a predetermined threshold. Alternatively, as would be appreciated by one of skill in the art, the computing hardware device 14 may also determine whether the rate of change exceeds and/or is equal to the threshold value. In accordance with an example embodiment of the present invention, the determination may be made by comparing the rate of change of the measurement values (e.g., $\sim$M) to a threshold variable X. The threshold variable X may represent a desired threshold of acceptability. As would be appreciated by one of skill in the art, the threshold variable X may be a value set by a user or an determined according to administrative guidelines. For example, the threshold variable may be set by company administration to be a value of 2 degree Fahrenheit per second. Accordingly, if the rate of change is less than the threshold value then the process progresses to step 264. Otherwise, if the rate of change exceeds the threshold value, the process returns to step 258 and repeats until the rate of change is less than the threshold. In accordance with an example embodiment of the present invention, if the rate of change is not less than the threshold value, in addition to returning to step 258, an alert may be triggered and displayed to a user of the probe device 12 that the rate of change is not less than the threshold value. As would be appreciated by one of skill in the art, the signal processing algorithm may process previous values of the rate of change of the measurement to determine whether or not to continue to step 264, or to return to step 258. For example, the signal processing algorithm may determine whether the temperature of the sample item or space modulates in accordance to a sine wave pattern.

At step 264, a determination is made that the correct steady state value for the received sample type, in that it is within the predetermined sample type range, has been detected. As would he appreciated by one of skill in the art, the rate of change as determined in steps 260 and 262 may establish a steady state measurement value as discussed with respect to step 208 of FIG. 2A. Once the correct measured value has been determined, then the measured value may be automatically recorded. At step 268, a determination is made (e.g. by computing hardware device 14) as to whether more sample types are to be measured. As would be appreciated by one of skill in the art, the determination may be made by checking a sample type checklist from the storage device 26 or may be determined by receiving an input from the user of the probe device 12, as discussed with respect to FIG. 2A. If it is determined that no more sample types are to be measured, then the process advances to step 270, at which the process terminates. Otherwise, if it is determined that more sample types need to be measured, the process returns to step 252 and repeats the steps of process 250.

FIG. 3 depicts an exemplary process for the operation of automatically determining when to measure and record the measured values of a sample item in accordance with aspects of the present invention. In particular, FIG. 3 depicts that the probe device 12 may automatically determine when to measure and record a measurement value of a sample item or space based on the use of one or more proximity sensors 18. As would be appreciated by one of skill in the art, the proximity sensors 18 may include a combination of transmitters (e.g., an NFC tag, laser sensors, IR sensors, sonic sensors, etc.), gesture recognition devices, and/or sensors (e.g., sensors 16) built into the probe device (e.g., ultrasound device). Additionally, one or more other sensors for measuring movement (e.g., accelerometer, gyroscope, etc.) of the probe device 12 may be used in place of or in combination with the proximity sensors 18. For example, a gyroscope may be used to determine when the probe device 12 is no longer moving and determine that the probe device 12, or the sensors 16, have been inserted into the sample item or space.

At step 310, the probe device 12 may receive proximity sensor data from the one or more proximity sensors 18 when the probe device 12 is within a predetermined distance of a target sample. In some implementations, the probe device 12 receives messages from a wireless beacon, such as a Bluetooth beacon that indicate proximity. For example, the one or more proximity sensors 18 may be located near a cooktop surface and the proximity sensor data received from the proximity sensors 18 may indicate that the probe device 12 is within range of the cooktop surface. In accordance with an example embodiment, the proximity sensor data may also indicate that the probe device 12 is within range of or has been inserted into a particular sample item type or space, having a predetermined range of sample physical measurement values (e.g., sample physical measurement values as discussed with respect to FIG. 2A). For example, when the probe device 12 is within range of a proximity sensor 18 for a cooktop, the proximity sensor data may indicate that the cooktop is used for cooking poultry, which has a predetermined temperature range of 165-170 degrees Fahrenheit. As would be appreciated by one of skill in the art, the proximity device may directly transmit the sample type information to the probe device 12 in the proximity sensor data, such that the probe device 12 automatically receives the item type to be measured. Alternatively, the one or more sensors 16 may transmit an identifier used by the probe device 12 to look up the appropriate sample type information in the storage device 26. For example, using the identifier, the probe device 12 may look up a sample type associated with the particular proximity sensor 18, and the predetermined measurement value ranges associated with that sample type.

At step 320, a user may physically insert the probe device 12 into the selected target sample item or space. For example, the user may inselt the temperature sensor (e.g., thermocouple) of the probe device 12 into a sample food item (e.g., poultry). As would be appreciated by one of skill in the art, the probe device 12, or the at least one or more sensors 16 may be configured to take a measurement without physically inserting the sensors 16. Into the sample item or space, as discussed with respect to FIG. 2A. Additionally, the proximity sensors 18 may be used to detect that the probe device 12 has been inserted into a sample item or space and whether the probe device has been inserted to a correct depth of the sample item or space. At step 330, the probe device 12 may detect a proximity sensor 18 and/or receive instructions from the proximity sensor 18 to initiate instructions to take a steady state measurement value within a predetermined range of the selected sample type. For example, the probe device 12 may determine that a particular proximity device is within range of or has been inserted into a sample item or space and initiate a measurement using one or more sensors 16. During the measurement, the probe device 12 may determine that the measured values are unchanging over a period of time and thus recognizes a steady state measured value. As would be appreciated by one of skill in the art, the detection of the steady state measurement value may be performed in manner similar to that discussed with respect to step 208 of FIGS. 2A and 2B.

At step 340, in response to determining a steady state measurement value within the predetermined range of the selected sample type indicated by the proximity sensor 18 (step 208), the probe device 12 may automatically record the steady state measurement value. For example, the steady state measurement value is recorded in the storage device 26 associated with the sample type item (e.g., poultry) associated with the detected proximity sensor 18. As would be appreciated by one of skill in the art, additional data and/or metadata may also be stored in the storage device 26. For example, the probe device 12 may also record a time at which the temperature was taken, the number and iteration of that particular sample type that has been taken, an employee identifier of the user taking the measurements, etc.

As would be appreciated by one of skill in the art, the probe device 12 may be configured to use a combination of detecting a change in temperature and the proximity sensors 18 to automatically measure and record temperatures of various items. For example, the probe device 12 may use a combination of the processes depicted in FIGS. 2 and 3 and additional methods known in the art.

Figure 4A:
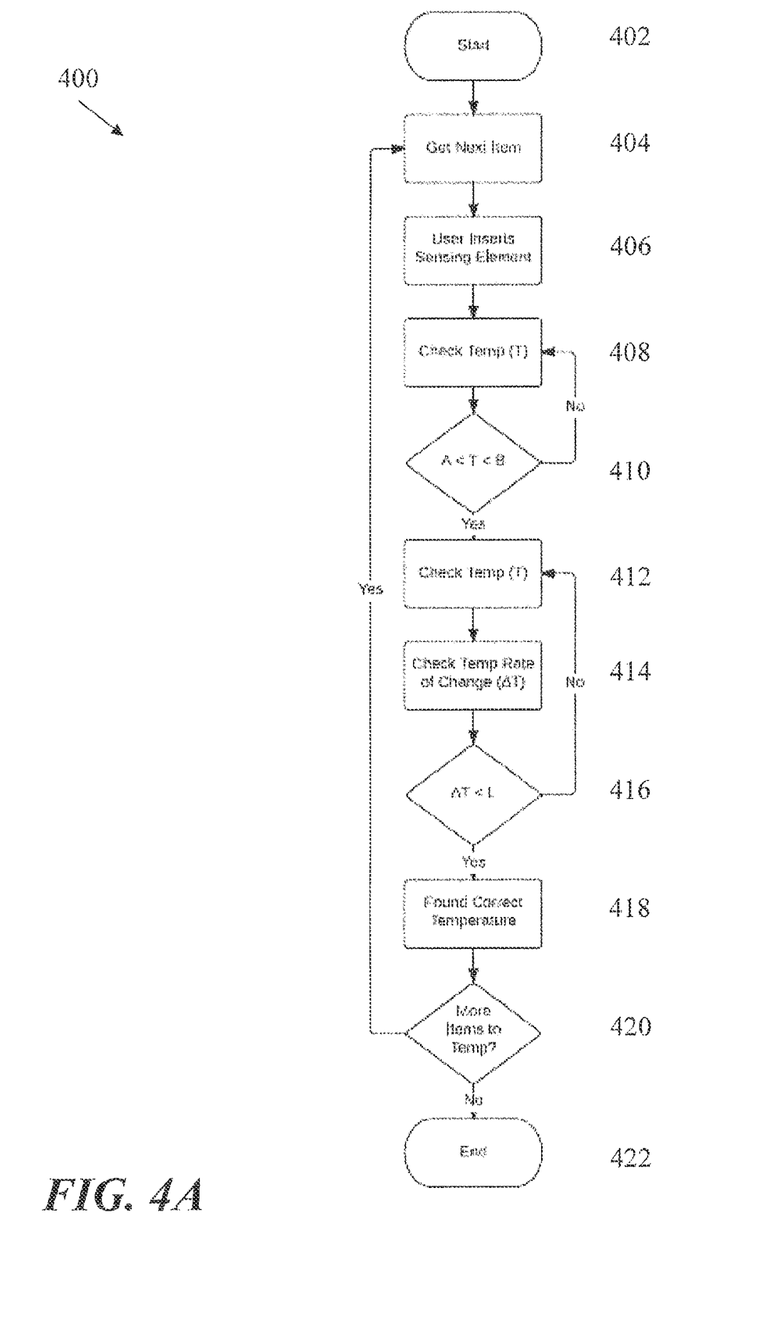
FIGS. 4A, 4B, and 4C are illustrative flowcharts depicting example methods for measuring and recording a temperature of one or more items or spaces, in accordance with aspects of the present invention.
Figure 4B:
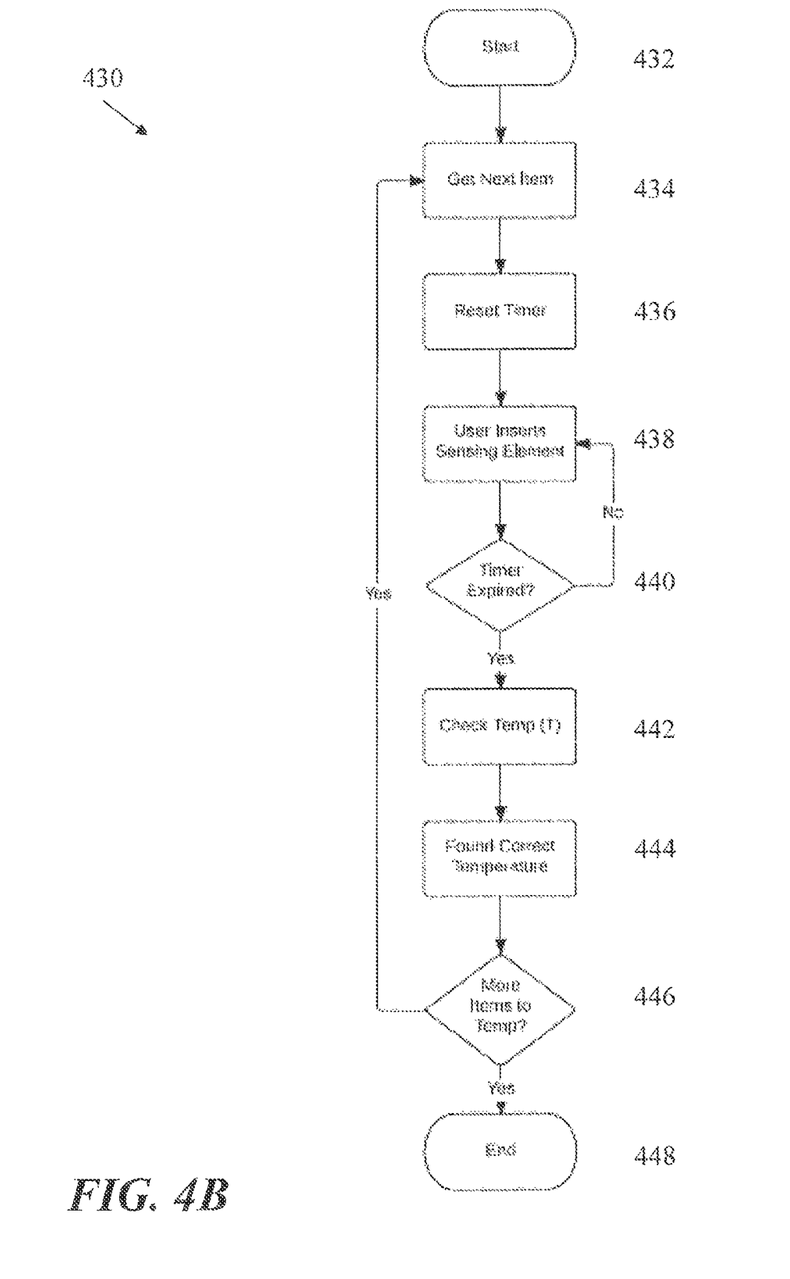
Figure 4C:
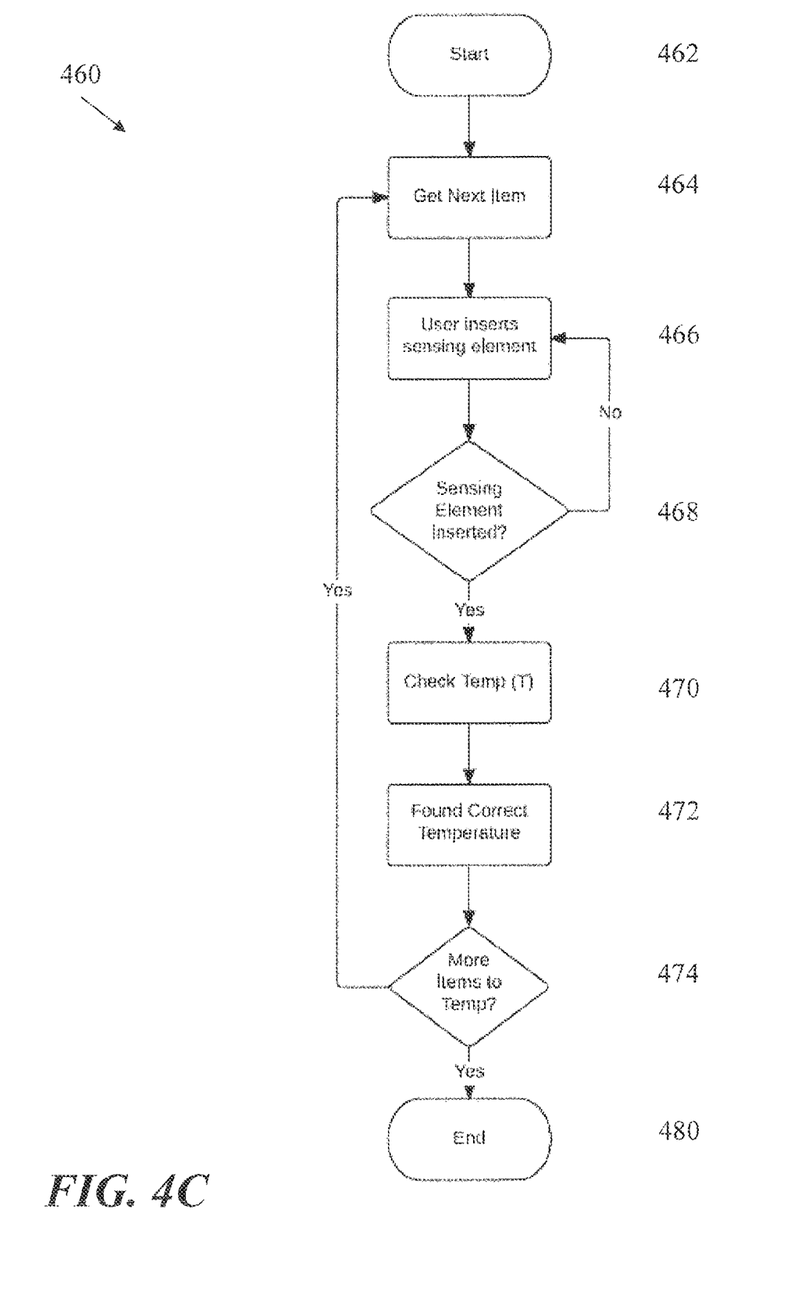

FIGS. 4A-4C depict methods of automatically measuring and recording temperatures of one or more sample items or spaces using a combination of steps discussed in FIGS. 2A, 2B, and 3, and in accordance with the present invention. In particular, the process 400 in FIG. 4A depicts an example method using the processing signal algorithm to automatically measure and record a temperature of one or more sample items (e.g., food items). At step 402, a user initiates the probe device 12 to take temperatures of one or more sample items using the probe device 12 or one or more sensors 16. At step 404, the next sample item to be measured is received by the probe device 12 (e.g., received as discussed with respect to FIGS. 1-3). At step 406, the user inserts (or aims) the probe device 12 into the sample item (e.g., as discussed with respect to FIGS. 1-3). At step 408, the probe device 12, or at least the sensors 16, measures the temperature of the sample item (e.g., as discussed with respect to FIGS. 1-3). At step 410, the probe device 12 determines whether the measured temperate falls within a predetermined range (e.g., between the predetermined values A and B) for the sample type of the sample item (e.g., as discussed with respect to FIGS. 1-3). If the measured temperature is within the predetermined range then the process advances to step 412, otherwise the process returns to step 408.

Continuing with FIG. 4A, at step 412, the temperature of the item is measured, as done in step 408. At step 414, the rate of change of the measured temperatures are determined by the probe device 12 (e.g., as discussed with respect to FIGS. 2A and 2B). At step 416, the probe device 12 determines whether the rate of change of the temperature (T) is less than a predetermined threshold value (L) (e.g., as discussed with respect to FIG. 2B). For example, if the rate of change of the temperature is less than the predetermined threshold value then the temperature has stabilized. If the rate of change of the temperature is less than the predetermined threshold value then the process advances to step 418, otherwise the process returns to step 412. At step 418, a determination that the correct temperature has been measured is made by the probe device 12 and the temperature is subsequently recorded. At step 420, the probe device 12 determines whether more temperature(s) of one or more sample items are to be taken. If the probe device 12 determines that more temperature(s) of one or more sample items are to be measured then the process returns to step 404 (e.g., as discussed with respect to FIGS. 2A and 2B), otherwise the process advances to step 422. At step 422, the process has completed and terminates.

The process 430 in FIG. 4B depicts an example method for displaying a timer to a user taking a temperature of one or more sample items. In particular, the process 430 depicts a method in which a timer is used to instruct a user to put the probe device 12, or the one or more sensors 16, into the correct item or space before the probe device 12 automatically takes and records a temperature of an item or space. At step 432, a user initiates the probe device 12 to take temperatures of one or more sample items using the probe device 12, or one or more sensors 16. At step 434, the next sample item to be measured is received by the probe device 12 (e.g., received as discussed with respect to FIGS. 1-3). At step 436, a timer is initialized and/or reset for the new received sample item. For example, the timer may be reset to 15 seconds to allow the user time to insert the probe device 12, or the one or more sensors 16, into the next sample item. As would be appreciated by one of skill in the art, the timer may be an incremental countdown timer or other timer known in the air. At step 438, the user inserts (or aims) the probe device 12 into the sample item (e.g., as discussed with respect to FIGS. 1-3).

Continuing with FIG. 4B, at step 440, the probe device 12 determines whether the time has expired. For example, the probe device 12 may determine whether the timer has reached 0 seconds. If the probe device 12 determines that the timer has expired, then the process advances to step 442, otherwise the process returns to step 438. At step 442, in response to the determination that the timer expired, instructions are triggered to take a temperature of the sample item. At step 444, a determination that the correct temperature has been measured is made by the probe device 12 and the temperature is subsequently recorded. At step 446, the probe device 12 determines whether more temperature(s) of one or more sample items are to be taken. If the probe device 12 determines that more temperature(s) of one or more sample items are to be measured, then the process returns to step 434 (e.g., as discussed with respect to FIGS. 2A and 2B), otherwise the process advances to step 448. At step 448, the process has completed and terminates.

The process 460 in FIG. 4C depicts an example method using the proximity sensors 18 as discussed with respect to FIG. 3. In particular, the process 460 depicts a method in which the probe device 12 automatically takes and records a temperature of an item using proximity sensors 18 (as discussed with respect to FIGS. 1 and 3). At step 462, a user initiates the probe device 12 to take temperatures of one or more sample items using the probe device 12, or one or more sensors 16. At step 464, the next sample item to be measured is received by the probe device 12 (e.g., received as discussed with respect to FIGS. 1-3). At step 466, the user inserts (or aims) the probe device 12 into the sample item (e.g., as discussed with respect to FIGS. 1-3). At step 468, the probe device 12 determines whether the one or more sensors 16 are inselied into the sample item, using the proximity sensors 18 and/or the one or more sensors 16 (as discussed with respect to FIGS. 1 and 3). If the probe device 12 determines that the one or more sensors 16 are inserted in the sample item, then the process advances to step 470, otherwise the process returns to step 466. Accordingly, the temperature of the item will not be measured (at step 470) until the probe device 12 determines that the one or more sensors 16 are inserted in the sample item.

At step 470, in response to the determination that the sensing element is inserted, instructions are triggered to take a temperature of the item. At step 472, a determination that the correct temperature has been measured is made by the probe device 12 and the temperature is subsequently recorded. At step 474, the probe device 12 determines whether more temperature(s) of one or more sample items are to be taken. If the probe device 12 determines that more temperature(s) of one or more sample items are to be measured then the process returns to step 464 (e.g., as discussed with respect to FIGS. 2A and 2B), otherwise the process advances to step 480. At step 480, the process has completed and terminates.

Figure 5:
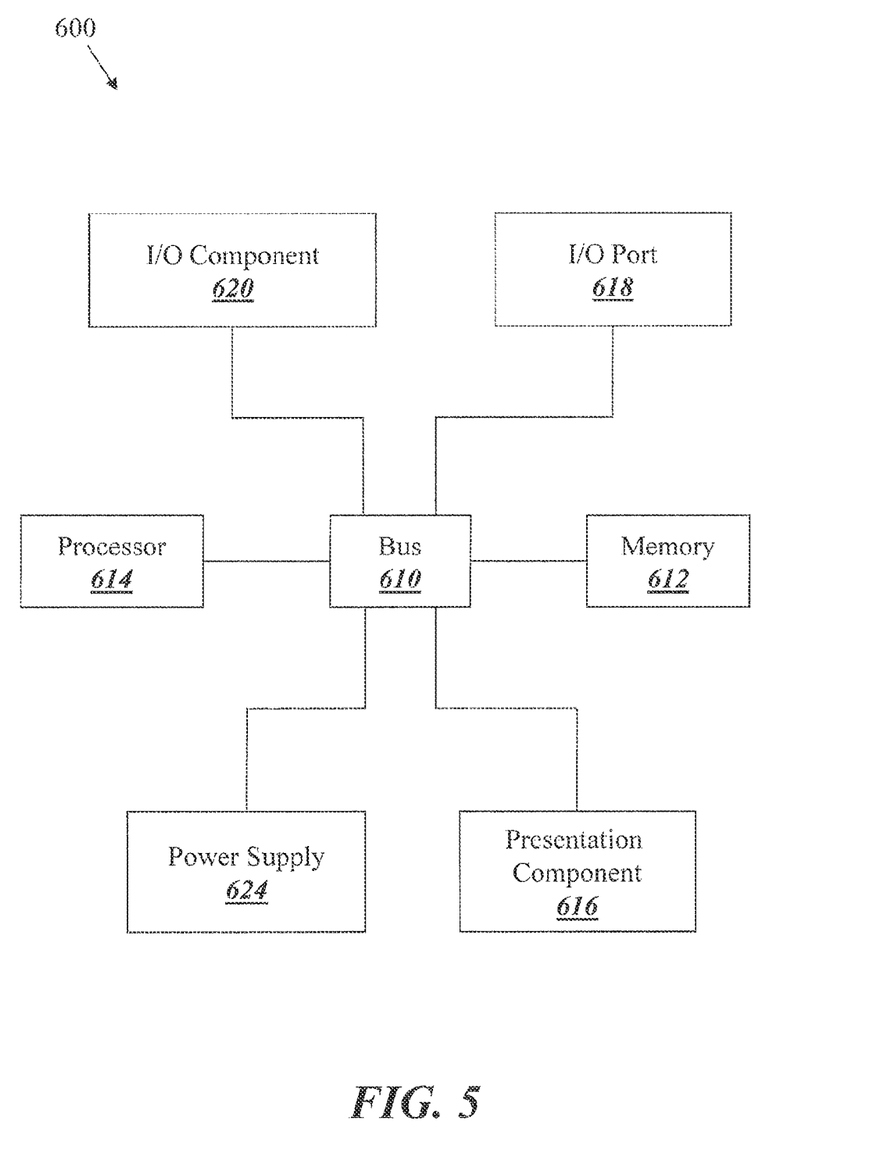
FIG. 5 is a diagrammatic illustration of a high level architecture for implementing processes in accordance with aspects of the present invention.

Any suitable computing device can be used to implement the probe device 12 and the computing hardware device 14 and methods/functionality described herein. One illustrative example of such a computing device 600 is depicted in FIG. 5. The computing device 600 is merely an illustrative example of a suitable computing environment and in no way limits the scope of the present invention. A "computing device," as represented by FIG. 5, can include a "workstation," a "server," a "laptop," a "desktop," a "hand-held device," a "mobile device," a "tablet computer," or other computing devices, as would be understood by those of skill in the art. Given that the computing device 600 is depicted for illustrative purposes, embodiments of the present invention may utilize any number of computing devices 600 in any number of different ways to implement a single embodiment of the present invention. Accordingly, embodiments of the present invention are not limited to a single computing device 600, as would be appreciated by one with skill in the art, nor are they limited to a single type of implementation or configuration of the example computing device 600.

The computing device 600 can include a bus 610 that can be coupled to one or more of the following illustrative components, directly or indirectly: a memory 612, one or more processors 614, one or more presentation components 616, input/output ports 618, input/output components 620, and a power supply 624. One of skill in the art will appreciate that the bus 610 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 5 is merely illustrative of an exemplary computing device that can be used to implement one or more embodiments of the present invention, and in no way limits the invention.

The computing device 600 can include or interact with a variety of computer readable media. For example, computer-readable media can include Random Access Memory (RAM); Read Only Memory (ROM); Electronically Erasable Programmable Read Only Memory (EEPROM); flash memory or other memory technologies; CD-ROM, digital versatile disks (DVD) or other optical or holographic media; magnetic cassettes, magnetic tape, magnetic disk storage or other magnetic storage devices that can be used to encode information and can be accessed by the computing device 600.

The memory 612 can include computer-storage media in the form of volatile and/or nonvolatile memory. The memory 612 may be removable, non-removable, or any combination thereof. Exemplary hardware devices are devices such as hard drives, solid state memory, optical-disc drives, and the like. The computing device 600 can include one or more processors that read data from components such as the memory 612, the various I/O components 616, etc. Presentation component(s) 616 present data indications to a user or other device. Exemplary presentation components include a display device, speaker, printing component, vibrating component, etc.

The I/O ports 618 can enable the computing device 600 to be logically coupled to other devices, such as I/O components 620. Some of the I/O components 620 can be built into the computing device 600. Examples of such I/O components 620 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without depailing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall there between.

What is claimed is:

1. A method performed by one or more electronic devices, the method comprising:
    accessing data indicating a series of measurements to be performed, wherein the series of measurements comprises at least one temperature measurement for each of multiple different items to be measured;
    receiving, by the one or more electronic devices, data indicating a measurement result for a first measurement in the series of measurements, wherein the first measurement is for an item of a first sample type, the measurement being performed using one or more sensors;
    determining, by the one or more electronic devices, that the measurement result satisfies a predetermined condition; and
    in response to determining that the measurement satisfies the predetermined condition:
        recording, by the one or more electronic devices, the measurement result as a measurement result for the first sample type, including recording the measurement result as a result for the first measurement in the series of measurements; and
        advancing, by the one or more electronic devices, to perform an additional measurement using the one or more sensors, including performing a subsequent measurement in the series of measurements using the one or more sensors.

2. The method of claim 1, wherein the series of measurements comprises measurements for multiple different sample types, and
    wherein advancing to perform a next measurement in the series of measurements comprises determining a sample type for the next measurement and one or more parameters associated with the sample type.

3. The method of claim 1, wherein recording the measurement result and advancing to perform another measurement are initiated automatically by the one or more electronic devices without input from a user in response to determining that the measurement satisfies the predetermined condition.

4. The method of claim 1, wherein the first measurement for the item of the first sample type is a first temperature measurement for a food item; and
    wherein the one or more sensors comprise a temperature probe.

5. The method of claim 1, wherein recording the measurement result comprises recording the measurement result in a temperature log for a restaurant.

6. The method of claim 1, wherein recording the measurement comprises sending data indicating the measurement result to a server over a network.

7. The method of claim 1, wherein the predetermined condition comprises a measured value for the measurement being stabilized.

8. The method of claim 1, wherein the predetermined condition comprises a measured value for the measurement being in a predetermined range.

9. The method of claim 1, wherein the measurement result is a measured temperature that is determined using the one or more sensors, and wherein the predetermined condition comprises the measured temperature being is greater a minimum temperature.

10. The method of claim 1, comprising providing, for display on a user interface, an ordered list of samples to measure using the one or more sensors.

11. The method of claim 1, comprising displaying, in a user interface, an indication of an acceptable temperature for the first sample type; and
    wherein the first measurement is a temperature measurement, wherein the additional measurement is a temperature measurement.

12. The method of claim 1, comprising:
    after advancing to perform the additional measurement:
        indicating, in a user interface, a sample type for the additional measurement;
        indicating, in the user interface, that the additional measurement is a temperature measurement; and displaying, in the interface, an acceptable range of temperatures for the sample type to be measured with the additional measurement.

13. The method of claim 1, wherein advancing to perform the additional measurement comprises displaying an instruction to a user for a next measurement to be performed using the device, where the instruction indicates a type of sample to be measured in the additional measurement.

14. The method of claim 7, wherein the measurement value is stabilized by changing at a rate that is less than a rate-of-change threshold.

15. The method of claim 8, wherein the first measurement is a temperature measurement for a sample, and wherein the predetermined range is a temperature range corresponding to the first sample type of the sample.

16. A system comprising:
one or more electronic devices; and
one or more computer-readable media storing software comprising instructions that are operable, when executed by one or more electronic devices, to cause the one or more electronic devices to perform operations comprising:
   accessing data indicating a series of measurements to be performed, wherein the series of measurements comprises at least one temperature measurement for each of multiple different items to be measured;
   receiving, by the one or more electronic devices, data indicating a measurement result for a first measurement in the series of measurements, wherein the first measurement is for an item of a first sample type, the measurement being performed using one or more sensors;
   determining, by the one or more electronic devices, that the measurement result satisfies a predetermined condition; and
   in response to determining that the measurement satisfies the predetermined condition:
      recording, by the one or more electronic devices, the measurement result as a measurement result for the first sample type, including recording the measurement result as a result for the first measurement in the series of measurements; and
      advancing, by the one or more electronic devices, to perform an additional measurement using the one or more sensors, including performing a subsequent measurement in the series of measurements using the one or more sensors.

17. One or more non-transitory computer-readable media storing software comprising instructions that are operable, when executed by one or more electronic devices, to cause the one or more electronic devices to perform operations comprising:
   accessing data indicating a series of measurements to be performed, wherein the series of measurements comprises at least one temperature measurement for each of multiple different items to be measured;
   receiving, by the one or more electronic devices, data indicating a measurement result for a first measurement in the series of measurements, wherein the first measurement is for an item of a first sample type, the measurement being performed using one or more sensors;
   determining, by the one or more electronic devices, that the measurement result satisfies a predetermined condition; and
   in response to determining that the measurement satisfies the predetermined condition:
      recording, by the one or more electronic devices, the measurement result as a measurement result for the first sample type, including recording the measurement result as a result for the first measurement in the series of measurements; and
      advancing, by the one or more electronic devices, to perform an additional measurement using the one or more sensors, including performing a subsequent measurement in the series of measurements using the one or more sensors.

18. The one or more non-transitory computer-readable media of claim 17, wherein recording the measurement result and advancing to perform another measurement are initiated automatically by the one or more electronic devices without input from a user in response to determining that the measurement satisfies the predetermined condition.

19. The one or more non-transitory computer-readable media of claim 17, wherein the first measurement for the item of the first sample type is a first temperature measurement for a food item; and
wherein the one or more sensors comprise a temperature probe.

20. The one or more non-transitory computer-readable media of claim 17, wherein the series of measurements comprises measurements for multiple different sample types, and
wherein advancing to perform a next measurement in the series of measurements comprises determining a sample type for the next measurement and one or more parameters associated with the sample type.

* * * * *